(12) United States Patent
Muyldermans et al.

(10) Patent No.: US 6,479,280 B1
(45) Date of Patent: Nov. 12, 2002

(54) RECOMBINANT PHAGES CAPABLE OF ENTERING HOST CELLS VIA SPECIFIC INTERACTION WITH AN ARTIFICIAL RECEPTOR

(75) Inventors: Serge Muyldermans, Hoeilaart (BE); Jan Steyaert, Beersel (BE); Karen Silence, Overijse (BE); Els Torreele, Brussels (BE)

(73) Assignee: Vlaams Interuniversitair Institutuut voor Biotechnologie VZW (BE)

( * ) Notice: Subject to any disclaimer, the term of this patent is extended or adjusted under 35 U.S.C. 154(b) by 0 days.

(21) Appl. No.: 09/433,404

(22) Filed: Nov. 3, 1999

(30) Foreign Application Priority Data

Sep. 24, 1999 (EP) .......................................... 99402348.9

(51) Int. Cl.⁷ ............................................... C12N 15/00

(52) U.S. Cl. ............................ 435/320.1; 435/5; 435/6; 435/173.3; 435/235.1; 536/23.1; 536/23.4; 536/23.72

(58) Field of Search ....................... 435/5, 6, 7.1, 173.3, 435/235.1, 320.1; 514/44; 530/388.1, 384.1; 536/23.1, 23.4, 23.72

(56) References Cited

U.S. PATENT DOCUMENTS

| | | | |
|---|---|---|---|
| 4,637,980 A | | 1/1987 | Auerbach et al. |
| 5,516,637 A | * | 5/1996 | Huang et al. ................. 435/6 |

FOREIGN PATENT DOCUMENTS

| | | |
|---|---|---|
| EP | 0 614 989 A1 | 9/1994 |
| RU | 2105064 | 2/1998 |
| WO | WO 90/01870 | 3/1990 |
| WO | WO 94/04678 | 3/1994 |
| WO | WO 95/04079 | 2/1995 |
| WO | WO 95/27043 | 10/1995 |
| WO | WO 97/10330 | 3/1997 |
| WO | WO 98/51318 | 11/1998 |
| WO | WO 99/34006 | 7/1999 |

OTHER PUBLICATIONS

Becerril et al., "Toward Selection of Internalizing Antibodies from Phage Libraries," 1999, *Biochem. Biophys. Res. Comun.*, 255(2): 386–393.

Beekwilder et al., "A phagemid vector using the *E. coli* phage shock promoter facilitates phage display of toxic proteins," 1999, *Gene*, 228: 23–31.

Cote–Sierra et al., "A new membrane–bound Oprl lipoprotein expression vector High production of heterologous fusion proteins in Gram (−) bacteria and the implications for oral vaccination," 1998, *Gene*, 221: 25–34.

Dall'Acqua and Carter, "Antibody engineering," 1998, *Curr. Opin. Struct. Biol.*, 8(4): 443–450.

de Bruin et al., "Selection of high–affinity phage antibodies from phage display libraries," 1999, *Nature Biotechnology*, 17: 397–399.

Deng et al., "Interaction of the Globular Domains of plll Protein of Filamentous Bacteriophage fd with the F–Pilus of *Escherichia coli*, " 1999, *Virology*, 253: 271–277.

De Vos et al., "Detection of the outer membrane lipoprotein I and its Gene in fluorescent and non–fluoroscent pseudomonads: implications for taxonomy and diagnosis," 1993, *J. Gen. Microbiol.*, 139: 2215–2223.

Drees, "Progress and variations in two–hybrid and three–hybrid technologies," 1999, *Curr. Opin. Chem. Biol.*, 3: 64–70.

Glahroudi et al., "Selection and identification of single domain antibody fragments from camel heavy–chain antibodies," 1997, *FEBS letters*, 414: 521–526.

Hamers–Casterman et al., "Naturally occurring antibodies devoid of light chains," 1993, *Nature*, 363: 446–448.

Hartley and Rogerson, "Production and Purification of the Extracellular Ribonuclease of *Bacillus Amyloliquefaciens* (Barnase) and its intracellular Inhibitor (Barstar)," 1972, *Prep. Biochem.*, 2(3): 299–242.

Jucovic and Hartley, "In vivo system for the detection of low level activity barnase mutants," 1995, *Protein Engineering*, 8(5): 497–499.

Krebber et al., "Selectively–infective Phage (SIP): A Mechanistic Dissection of a Novel in vivo Selection for Protein–ligand Interactions," 1997, *J. Mol. Biol.*, 268: 607–618.

Lauwereys et al., "Potent enzyme inhibitors derived from dromedary heavy–chain antibodies," 1998, *EMBO J.* 17(13): 3512–3520.

Malmborg et al., "Selective Phage Infection Mediated by Epitope Expression on F Pilus," 1997, *J. Mol. Biol.*, 273(3): 544–551.

Maurer et al., "Autodisplay: One–Component System for Efficient Surface Display and Release of Soluble Recombinant Proteins from *Escherichia coli*," 1997, *J. Bacteriol.*, 179(3): 794–804.

Montag et al., "Receptor–recognizing Proteins of T–even Type Bacteriophages," 1987, *J. Mol. Biol.*, 196: 165–174.

Montag et al., "Receptor–recognizing Proteins of T–even Type Bacteriorphages," 1990, *J. Mol. Biol.*, 216: 327–334.

Poul and Marks, "Targeted Gene Delivery to Mammalian Cells by Filamentous Bacteriophage," 1999, *J. Mol. Biol.*, 288: 203–211.

(List continued on next page.)

Primary Examiner—Jeffrey Stucker
Assistant Examiner—Ulrike Winkler
(74) Attorney, Agent, or Firm—Fish & RIchardson, P.C., P.A.

(57) ABSTRACT

The invention relates to a genetically modified bacteriophage, pseudovirion or phagemid capable of entering a host cell by binding of its artificial ligand to an artificial receptor present on said host cell. The invention relates also to the use of the genetically modified bacteriophage, pseudovirion or phagemid and of the host cell to screen sequence libraries, including antibody library.

10 Claims, 4 Drawing Sheets

OTHER PUBLICATIONS

Rodi and Makowski, "Phage–display technology—finding a needle in a vast molecular haystack," 1999, *Curr. Opin. Biotechn.*, 10(1): 87–93.

Sever et al., "The study of the mutation affecting the rate of synthesis of *Escherichia coli* RNA polymease ββ' subunits," 1982, *Genetika*, 18(6): 947–955 (abstract only).

Skerra and Plückthun, Assembly of a Functional Immunoglobulin $F_V$ Fragment in *Escherichia coli*, 1988, *Science*, 240: 1038–1041.

Smith et al., "The Control of Experimental *Escherichia coli* Diarrhoea in Calves by Means of Bacteriophages," 1987, *J. Gen. Microbiol.* 133: 1111–1126.

Spada et al., "Selectively Infective Phages (SIP)," 1997, *Biol. Chem.*, 378(6): 445–456.

Wang et al., "Cloning of the J gene of bacteriophage lambda, expression and solubilization of the J protein: first in vitro studies on the interactions between J and LamB, its cell surface receptor," 1998, *Res. Microbiol.*, 149: 611–624.

Werts et al., "Adsorption of Bacteriophage Lambda on the LamB Protein of *Escherichia coli* K–12: Point Mutations in Gene J of Lambda Responsible for Extended Host Range," 1994, *J. Bacteriol.* 176(4): 941–947.

Williams and Meynell, "Female–Specific Phages and F–Minus Strains of *Escherichia coli* K12," 1971, *Mol. Gen. Genet.* 113: 222–227.

* cited by examiner

Figure 1:
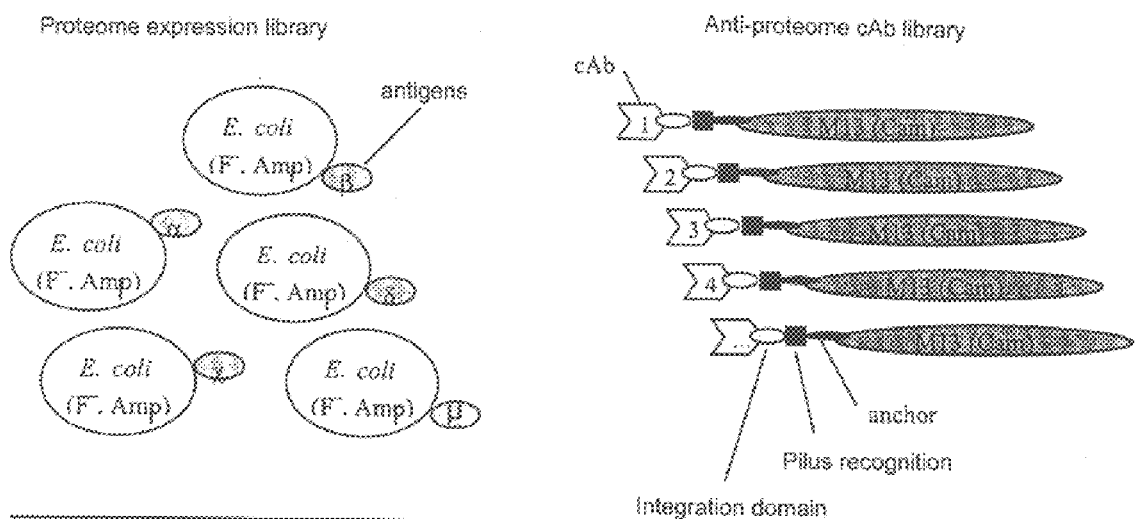

Figure 1: outline of the screening of an antigen - antibody library

*Phagemid : pK7C3*

*Ptrc-OprI*

Figure 4: Results Western blot

Expression of ovalbumin on the surface of the *E.coli* membrane

| 64 |
| 52 |
| 39 |
| 26 |
| 21 |
| 15 |

| 9 |

LB  M9   LB   M9
‾‾‾‾‾‾   ‾‾‾‾‾‾‾
OprIp    OprIp-ova

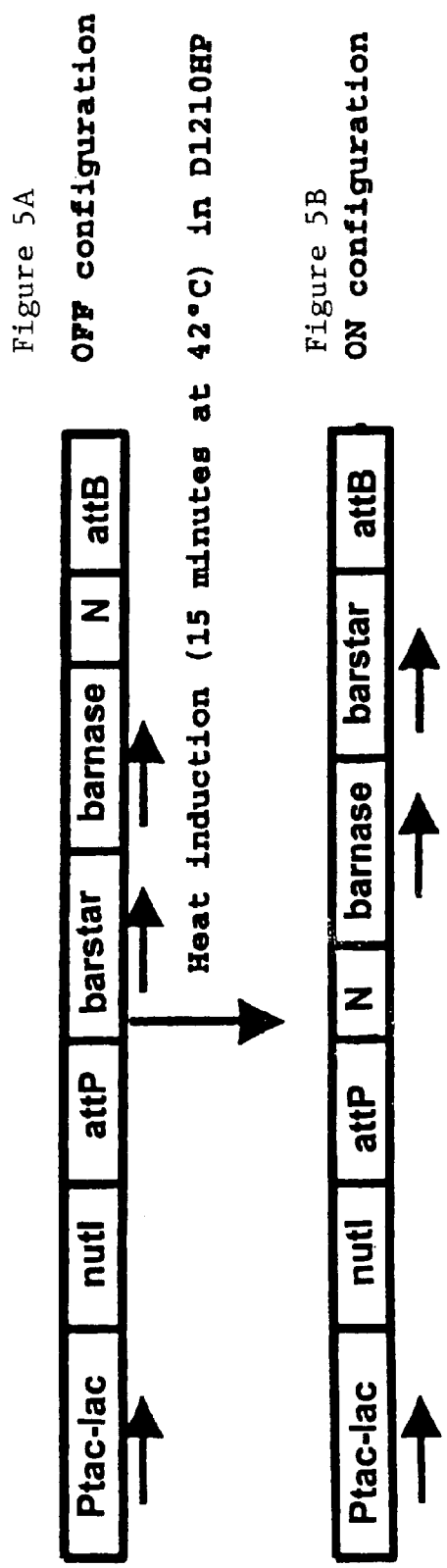

SEQUENCE LISTING

<160> NUMBER OF SEQ ID NOS: 3

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
catgcgatga ctcgcggccc agccggccat ggc                33

<210> SEQ ID NO 2
<211> LENGTH: 30
<212> TYPE: DNA
<213> ORGANISM: Artificial Sequence

```
<220> FEATURE:
<223> OTHER INFORMATION: primer

<400> SEQUENCE: 2
gtgtgcggcc gctgaggaga crgtgaccwg                                      30

<210> SEQ ID NO 3
<211> LENGTH: 124
<212> TYPE: PRT
<213> ORGANISM: Camel

<400> SEQUENCE: 3

Asp Val Gln Leu Val Glu Ser Gly Gly Ser Val Pro Ala Gly Ser
 1               5                  10                  15

Leu Arg Leu Ser Cys Ala Val Ser Gly Tyr Thr Tyr Glu Asn Arg Tyr
                20                  25                  30

Met Ala Trp Phe Arg Gln Ala Pro Gly Lys Glu Arg Glu Gly Val Ala
             35                  40                  45

Ala Ile Trp Arg Gly Gly Asn Asn Pro Tyr Tyr Ala Asp Ser Val Lys
         50                  55                  60

Gly Arg Phe Thr Ile Ser Gln Asp Asn Ala Lys Asn Ile Val Ser Leu
 65                  70                  75                  80

Leu Met Asn Ser Leu Lys Pro Glu Asp Thr Ala Ile Tyr Tyr Cys Ala
                 85                  90                  95

Ala Gln Ala Gly Arg Phe Ser Gly Pro Leu Tyr Glu Ser Thr Tyr Asp
             100                 105                 110

Tyr Trp Gly Gln Gly Thr Gln Val Thr Val Ser Ser
            115                 120
```

RECOMBINANT PHAGES CAPABLE OF ENTERING HOST CELLS VIA SPECIFIC INTERACTION WITH AN ARTIFICIAL RECEPTOR

The present invention relates to a recombinant bacteriophage, pseudovirion or phagemid that is capable of entering bacteria by specific binding to an artificial receptor. Said receptor does not comprise at its active binding site elements such as proteins or peptides that are derived from the natural receptor used in the specific initial bacteriophage-bacterium interaction.

BACKGROUND OF THE INVENTION

Bacteriophages, like bacteria, are very common in all natural environments. Bacteriophages (phages) are intracellular parasites. Bacteria and their phages have a common evolutionary history and phages may have adapted to their host species by multiple mechanisms. The phage genome may consist of double-stranded DNA, single-stranded DNA, double-stranded RNA or single-stranded RNA. Bacteriophages exist in several morphologies and can be spherical, cubic, filamentous, pleomorphic or tailed. Based on their life cycle, bacteriophages can be divided into three groups: the virulent phages capable of only lytic propagation (called lytic phages), the so-called temperate phages capable of either lytic propagation or lysogenic phase and the non-lysing phages where the mature phage is continuously extruded. The virulent life cycle of wild type phages consists of infection of the host cell, i.e. attachment to a specific receptor in the bacterial cell wall, followed by entering of the phage genome in the cell, replication of the phage genome, production of the phage structural components, phage assembly and release of the progeny phages after lysis of the host cell. In the lysogenic life cycle, the phage genome exists as a prophage resulting in coexistence of phage and host cell without lysis. Usually, this is achieved by integration of the phage genome into the bacterial chromosome. The life cycle of the non-lysing phages, like e.g. Bacteriophage M13, is similar to that of the lytic phages, but the infection is not followed by lysis. Bacteriophages have been extensively used in biotechnology. Phage genes or complete phages may be used to obtain lysis and/or killing of bacteria.

U.S. Pat. No. 4,637,980 describes the use of an *E. coli* strain containing defective temperature sensitive lambda lysogens as a method for cell disruption. Smith and coworkers (Smith et al., 1987, *J. Gen Microbiol.* 133; 1111–1126) describe the use of bacteriophages to treat diarrhea in calves, caused by seven different bovine enteropathogenic strains of *E. coli* WO95/27043 describes a method to treat infectious diseases caused by several bacterial genera, such as Mycobacterium Staphylococcus, Vibrio, Enterobacter, Enterococcus, Eschericia, Haemophilus, Neisseria, Pseudomonas, Shigella, Serratia, Salmonella and Stretococcus, comprising the administration of bacteriophages with delayed inactivation by the animal host defence system. WO98/51318 describes a diagnostic kit and a pharmaceutical composition, comprising bacteriophages to diagnose and to treat bacterial diseases caused by bacteria, such as Listeria, Klebsielia, Pneumococcus, Moraella, Legionelle, Edwardsiella, Yersinia, Proteus, Heliobacter, Salmonella, Chlamrydia, Aeromonas and Renibacterium.

Another application of bacteriophages is the in vitro selection of proteins displayed on the tip of filamentous phages on immobilised target (=biopanning), which is a powerful technique for the isolation of interacting protein-ligand pairs from large libraries, such as antibody libraries (for a recent review: Rodi and Makowski, 1999, *Curr. Opin. Biotechn.*, 10: 87–93). However, for optimal in vitro biopanning, a purified target protein is needed. Moreover, high quality of the library is a prerequisite for success. Enrichment for selfligated vector, phages carrying incomplete sequences, incorrect reading frames, deletions and amber stop codons are very often observed (Beekwilder et al, 1999, *Gene*, 228, 23–31 and de Bruin et al, 1999, *Nature Biotechnology*, 17: 397–399). In the search to avoid the problems encountered with panning using imperfect libraries, several alternative techniques, both bacteriophage based and non bacteriophage based, have been developed. Non bacteriophage based techniques are, amongst others ribosome display (Dall'Acqua and Carter, 1998, *Curr. Opin. Struct. Biol.*, 8: 443–450) and the yeast two-hybrid system (Drees, 1999, *Curr. Opin. Chem. Biol.*, 3: 64–70). Bacteriophage based techniques comprise display on phage lambda, SIP (Spada and Pluckthun, 1997, *Biol. Chem.*, 378: 445–456; EP0614989) and CLAP (Malmborg et al, 1997, *J. Mol. Biol.*, 273: 544–551; WO9710330). SIP and CLAP are in vivo selection techniques and have the advantage that the F+*E.coli* host cells can only be infected by bacteriophages or pseudovirions when a matched pair is formed. Both systems are based on the fact that pilin on the F-pili of *E.coli* cells serve as the natural receptor for binding of the D2-domain of pill from the phage (Deng et al., 1999, *Virology*, 253:271–277). This results in retraction of the pilus, so that an interaction between the D1 domain of pill with the TOL protein complex located in the *E.coli* cell membrane leads to the infection (Deng et al, 1999, *Virology*, 253: 271–277). SIP has the disadvantage that it only works for high affinities of the binding pairs and that each target needs to be cloned, expressed and purified as a fusion with the D2 domain of pill. Therefore, with SIP, normally only one target can be screened at the time. For CLAP only small peptides (15–18 amino acids) can be expressed on the F-pilus, hence, this technique can only be used for small linear epitopes. An additional disadvantage is the need for modified M13 to avoid natural infection of host cells. Therefore, removal of the D2 domain of pill is essential. This results in a truncated form of M13 and concomitant difficulties to obtain good titres.

It is known that bacteriophages use specific receptors on the host cell wall as a way to recognise the host cell and to start the infection process. In all the applications cited above, the propagation of phages, pseudovirions or phagemids is dependent on the use of the natural phage receptor, or part of it, on the host cell wall. For M13, mainly used in these systems, the natural receptor is pilin (Malmborg et al., 1997, *J. Mol. Biol.* 273: 544–551). Other examples of natural receptors are lamB for bacteriophage lambda (Werts et al, 1994, *J. Bacteriol.* 176: 941–947), the outer membrane protein OmpA for bacteriophages K3, Ox2 and M1 (Montag et al, 1987, *J. Mol. Biol.*, 196: 165–174), the outer membrane proteins OmpF and Ttr for bacteriophage T2 (Montag et al, 1987, *J. Mol. Biol.*, 196, 165–174), the outer membrane protein OmpC for the T4 phage family (T4, Tula, Tulb) (Montag et al.,1990, *J. Mol. Biol.*, 216: 327–334). The T4 bacteriophage family is using a C-terminal region of protein 37 as natural ligand (Montag et al., 1990, *J. Mol. Biol.*, 216: 327–334), bacteriophages T2, K3, Ox2 and M1 are using protein 38 as natural ligand (Montag et al, 1987, *J. Mol. Biol.*, 196, 165–174) whereas phage lambda is using the C-terminal portion of the lambda tail fibre protein as natural ligand (Wang et al., 1998, *Res. Microbiol*, 149: 611–624). Bacteriophage—receptor independent phage binding to mammalian cells expressing the growth factor receptor ErbB2 followed by receptor mediated endocytosis was also described: Marks and collaborators (Poul and Marks, 1999, *J. Mol Biol.*, 288: 203–211 and Becceril and Marks, 1999, *Biochem. Biophys. Res. Commun.*, 255: 386–393) successfully isolated phage capable of binding mammalian cells expressing the growth factor receptor ErbB2 and undergoing receptor mediated endocytosis by selection of a phage antibody library on breast tumour cells and recovery of infectious phage from within the cell. However, the phage could not propagate in the mammalian cell, and the detection of the cells carrying bacteriophage could only be realised in an indirect way, by expression green fluorescent protein as a reporter gene.

SUMMARY OF THE INVENTION

One aspect of the invention is a genetically modified bacteriophage, pseudovirion or phagemid that is not dependent upon its natural receptor or parts thereof for entering a host cell.

Another aspect of the invention is a genetically modified bacteriophage, pseudovirion or phagemid capable of entering a host cell by specific binding to an artificial receptor. These artificial receptors can be endogenous host cell proteins located at the bacterial surface, or parts thereof, that are normally not involved in the bacteriophage—bacterium interaction, but it may also be heterologous proteins, preferentially fusion proteins displaying an oligo- or polypeptide on the bacterial surface. The genetically modified bacteriophage, pseudovirion or phagemid binds to the artificial receptor preferentially by an artificial ligand. A specific embodiment is a genetically modified bacteriophage that is not dependent upon OmpA, OmpC, OmpF, Ttr or pilin for interaction with and/or entering *E.coli*. A further specific embodiment is a genetically modified M13 bacteriophage, pseudovirion or phagemid that does not depend upon pilin, or fragments thereof for specific interaction with and/or entering of *E. coli*. Said M13 bacteriophage, pseudovirion or phagemid can enter,both F⁺and F⁻*E. coli* cells, dependent upon an artificial receptor that is displayed on the surface of said cells.

Still another aspect of the invention is a bacteriophage, pseudovirion or phagemid that enters the host cell mediated by an antigen—antibody reaction, whereby in the binding complex no proteins or parts of the natural receptor are involved.

A preferred embodiment of the invention is a genetically modified M13 phage, pseudovirion or phagemid displaying an antibody, preferentially the variable part of a camel heavy chain antibody for instance disclosed in international patent application WO94/04678 and in Hamers-Casterman C et al Nature,vol 363, Jun. 3, 1993.p 446–448, on its tip, which can enter an *E.coli* host cell, displaying the antigen, preferentially as an pOprl fusion protein. The use of Oprl as a protein for the expression of an amino acid sequence at the surface of the cell wall of a host cell is disclosed for example in international patent application WO95/04079 which is incorporated herewith by reference.

A further aspect of the invention is the use of said bacteriophage, pseudovirion or phagemid for selective entering of a subpopulation of bacteria. Using the specific artificial receptor interaction, in a mixed culture, the bacteriophage, pseudovirion or phagemid will only enter those bacteria that carry said artificial receptor. By this, the subpopulation of bacteria can be identified and/or eliminated. One embodiment of the invention is the specific elimination of pathogenic bacteria by directing a recombinant bacteriophage, pseudovirion or phagemid to a specific bacterial surface protein of said pathogenic bacteria. The pathogenic bacteria can be gram positive, gram negative or gram variable and can belong, amongst other to the genera Aeromonas, Chiamydia Edwardsiella, Enterobacter, Enterococcus, Eschedchia, Haemophilus, Heliobacter, Klebsiella, Legionella, Listeria, Moraxella, Mycobacterium, Neisseria, Pneumococcus, Proteus, Pseudomonas, Renibacterium, Salmonella, Sernatia, Shigella, Staphylococcus, Vibrio or Yersinia, without that this summation is limitative.

Elimination can be obtained by the lytic cycle of the bacteriophage, but is not limited this method. Other methods of eliminating the host cell may be the production of a toxic product encoded by the recombinant bacteriophage genome in the host cell. A preferred embodiment is the production of barnase placed after an inducible promoter, such as the barnase—barstar cassette described by Jucovic and Hartley (*Protein engineering*, 8: 497–499, 1995).

Another aspect of the invention is a host cell, entered by the genetically modified bacteriophage, pseudovirion or phagemid. Such host cell comprises the nucleotide sequence encoding the artificial receptor and the nucleotide sequence encoding the artificial ligand. Such sequences may be expressed in the host cell in combination with marker sequences, especially sequences encoding antibiotic resistance genes. A preferred embodiment is an *E. coli* cell, preferentially transformed with a plasmid encoding a pOprl-fusion protein, more preferentially transformed with a plasmid derived from ptrc-Oprl, carrying a genetically modified M13 phage, pseudovirion or phagemid, preferentially a pK7C3 derived phagemid, wherein said genetically modified M13 phage is modified, especially by in vitro construction, with a nucleotide sequence encoding a protein capable of specifically binding to the pOprl-fusion protein.

In a particular embodiment of the invention, the Oprl-fusion protein is carried out in introducing the nucleotide sequence of the fusion partner acting as the region for interaction with the ligand expressed on the bacteriophage, pseudoviron or phagemid, especially as disclosed in WO95/04678.

Still a fiber aspect of the invention is the use of said bacteriophage, pseudovirion or phagemid to identify interacting proteins, including cases where none of the members of the interacting protein is kaown.

In different embodiments, the bacteriophage, pseudovirion or phagemid can be used to screen (1) a host cell, displaying a bait against a library of bacteriophages, pseudovirions or phagemids displaying the prey, (2) a bacteriophage, pseudovirion or phagemid displaying a bait against a library of host cells displaying the prey, (3) a library of bacteriophages, pseudovirions or phagemids displaying different preys or baits against a library of host cells, displaying different baits or prey (As illustrated in FIG. 1).

A preferred embodiment is where pOprl is used as fusion partner for the display of bait or prey on the surface of the F⁻*E.coli* strains (Williams & Meynell 1971. Mol. Gen. Genet. 113: 222–227) such as DH5α and UT5600 as host cell and where the phagemid pK7C3 is used for cloning the prey or bait as a pill fusion protein.

Another embodiment of the invention is the construction of a subtraction library, with the use of lytic bacteriophages, preferentially barnase expressing bacteriophages. In this embodiment, a part of the host cell library is recognised by lytic phages such as barnase expressing phages and killed upon recognition of the artificial receptor by the artificial ligand, entering of the bacteriophage, pseudovirion or phagemid and expression of the lytic gene. Another aspect of the invention is a method for selecting artificial receptor—artificial ligand interactions, comprising growing a host cell or a mixture of host cells displaying one or more artificial receptors, contacting said host cell or said mixture with a genetically modified bacteriophage, pseudovirion or phagemid or a mixture of genetically modified bacteriophages, pseudovirions or phagemids with one or more artificial ligands, selecting those cells that have been entered by one or more bacteriophages, pseudovirion of phagemid.

One embodiment of the invention is said method, whereby the selection is based on an antibiotic resistance marker. Another embodiment is said method whereby the cells are selected by killing of the host cell, preferentially by expression of barnase. A preferred embodiment is said method, whereby the host cell is an *E. coli* cell, displaying the artificial receptor as a pOprl fusion protein, and the genetically modified bacteriophage, pseudovirion or phagemid is a genetically modified M13, displaying an artificial ligand as a pill fusion protein.

DEFINITIONS

The following definitions are set forth to illustrate and define the meaning and scope of the various terms used to describe the invention herein.

Genetically modified bacteriophage: a bacteriophage of which the genome has been modified, at least by the introduction of the gene encoding for an artificial ligand. This introduction can be as a replacement of one of the endogenous genes or as an additional gene besides the endogenous genes.

Natural receptor: protein domain, protein or protein complex situated on the host cell wall, involved in the natural initial interaction between a bacteriophage and said host cell, whereby this interaction is followed by introduction of the genetic material of the bacteriophage into the host cell.

Artificial receptor: protein domain, protein, fusion protein or protein complex on the host cell wall whereby said protein domain, protein, fusion protein or protein complex does not contain one or more peptide fragments of at least 10 contiguous amino acids derived from the natural bacteriophage receptor in the protein sequence or region that is involved in the interaction between bacteriophage, pseudovirion or phagemid and the artificial receptor.

Protein : encompasses peptide, protein, glycoprotein, lipoprotein or another form of modified protein, including chemically modified protein.

Protein complex: protein—protein complex, but also protein—compound complex, whereby said compound may be any chemical or biological compound, including simple or complex inorganic or organic molecules, peptidomimetics, carbohydrates, nucleic acids or derivatives thereof.

Natural ligand: protein, protein domain or protein complex of the bacteriophage, pseudovirion, or phagemid involved in the natural initial interaction between said bacteriophage, pseudovirion, or phagemid, and a host cell, including recognition of and possibly binding to the natural receptor, whereby this interaction is followed by introduction of the genetic material of the bacteriophage into the host cell.

Artificial ligand: protein, protein domain or protein complex of the bacteriophage, pseudovirion, or phagemid, whereby said protein domain, protein, fusion protein or protein complex does not contain one or more peptide fragments of at least 10 contiguous amino acids derived from the natural ligand of the bacteriophage in the protein sequence or region that is involved in the interaction between bacteriophage, pseudovirion or phagemid and the artificial receptor.

Host cell: any bacterial cell that can allow a bacteriophage, pseudovirion or phagemid to enter said cell after interaction of a said bacteriophage, pseudovirion or phagemid with a natural or artificial receptor. As example, host cells include gram-negative or gram-positive bacteria, especially including *E coli* cells and in particular F⁻cells which do not permit entering of bacteriophages, pseudovirions or phagemids through the pillin mechanism.

Entering bacteria: means that the bacteriophage, pseudovirion or phagemid can enter as a whole or as a part (e.g. only the genetic material) the host cell after specific binding to the artificial receptor. The mechanism by which the material is entering the host cell is not limited to specific ways and can be amongst others an active infection process or a passive uptake by the host cell. Methods for determination of the specific binding of the artificial ligand with the artificial receptor are illustrated in the examples.

Specific binding: means that the initial step of the entering is mediated by a specific interaction between the artificial receptor on the host cell wall and the artificial ligand of the bacteriophage, pseudovirion or phagemid. This specific interaction is preferentially a protein—protein interaction. This entering after specific interaction should be distinguished from the Calcium dependent pilus independent infection that can be detected with M13 bacteriophages in which the second N-terminal domain of gIIIp has been removed (Krebber et al., 1997, *J. Mol. Biol.* 268: 607–618).

According to particular embodiments, the invention relates to a genetically modified host cell, transformed with a nucleotide sequence encoding an artificial receptor in conditions enabling that the artificial receptor be expressed at the surface of the host cell, said host cell being further transformed with a nucleotide sequence encoding said artificial ligand whereby said nucleotide sequence encoding the ligand entered the host cell as a consequence of the interaction between said artificial ligand and a protein sequence or region on said artificial receptor.

Particular genetically modified host cells are those wherein the nucleotide sequence encoding the artificial receptor and/or the nucleotide sequence encoding the artificial ligand are not initially known.

According to another specific embodiment, the genetically modified host cell is a gram-negative bacterium, especially an *E coli* cell of the F⁻type.

According to another particular embodiment, the genetically modified host cell is a transformed cell wherein the nucleotide sequences of the artificial receptor and the nucleotide sequence for the artificial ligand are respectively coding sequences of an antibody or a functional fragment thereof and coding sequence of an antigen, or are respectively coding sequences of an antigen and coding sequence of antibody or a functional fragment thereof.

In said genetically modified host cell of the invention, the functional antibody fragment can be a variable fragment of an antibody, encompassing four-chain antibodies or two-chain antibody as defined in international patent application WO 94/04678, including native or modified, especially truncated chains thereof. In a preferred embodiment the variable chain is a VHH fragment of a camelid antibody or a functional portion of said VHH, as disclosed in the above cited patent application which is incorporated by reference.

The invention relates also to the above defined genetically modified host cell, wherein the nucleotide sequence encoding the artificial receptor comprises a sequence encoding Oprl or a part of Oprl sufficient to enable the exposure, at the surface of the host cell, of a protein sequence or region capable of interacting with the artificial ligand.

A further object of the invention is a kit comprising a genetically modified host cell according to the above proposed definitions and specific embodiments or comprising a host cell and/or a bacteriophage, pseudovirion or phagemid and/or means including a cloning vector enabling the construction of said host cell and/or a bacteriophage, pseudovirion or phagemid according to the above definitions. A particular kit is designed to be used for in vivo panning of antibody or antibody fragment library, or antigenic sequences library.

Said kit can also be used for the simultaneous in vivo panning of both an antibody fragment library, and an antigenic'sequences library.

The invention therefore provides means for the identification of target sequences or molecules including especially amino acid sequences capable of interacting with a determined receptor, whether the nature or sequences of said receptor is known or unknown. Especially the invention can be used for the identification of therapeutic targets.

SHORT DESCRIPTION OF THE FIGURES

FIG. 1 dives a schematic representation of the screening of a proteome expression library against a camel VHH anti-proteome antibody library.

Figure 2:
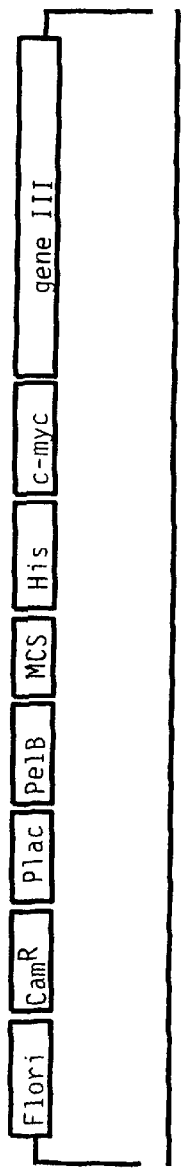

FIG. 2: schematic representation of phagemid pK7C3.

Figure 3:
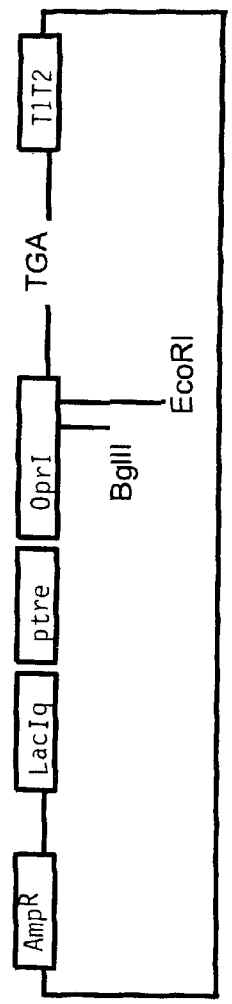

FIG. 3: schematic representation of plasmid ptrc-Oprl

FIG. 4: Results of the Western blot. From left to right: lane 1 shows the molecular weight markers. Lane 2 and 3 show the total lysate of *E. coli*, transformed with ptrc-Oprl, respectively after growth in LB (lane 2) and M9 (lane 3). Lane 4 and 5 show the total lysate of *E. coli*, transformed with ptrc-Oprl- OVA, respectively after growth in LB (lane 4) and M9 (lane 5). Proteins are visualised with anti-Oprl, as described in example II.

FIGS. 5 (*a* and *b*): Schematic representation of barnase activation by inversion of the expression cassette, due to integrase activity induced by heat shock.

EXAMPLES

Example I

Construction of M13 Pseudovirions Displaying Camel Heavy Chain Antibodies (VHH)

Immunisation of Camels

A camel (B) was immunised with 1 mg hen-egg ovalbumin (Sigma) in the presence of complete Freund adjuvant, and boosted in the presence of incomplete Freund adjuvant at days 7,14, 28, 35 and 42.

Anticoagulated blood was collected for lymphocyte isolation on day 45. This results in VHH library CAMELB
Construction of Phagemid Library Peripheral blood lymphocytes were prepared using Unisep (WAK Chemie, Germany). The camelid heavy chain antibodies (VHH's) from $10^7$ lymphocytes were cloned after RT-PCR amplification in the Ncol-Notl site of the pK7C3 vector (FIG. 2) and transformed in TG1 (Lauwereys et a/, 1998, the *EMBO Journal*, 17: 3512–3520). The primers for the amplification are.

CATGCGATGACTCGCGGCCCAGCCGGCCATGGC SEQ ID NO: 1 and
GTGTGCGGCCGCTGAGGAGACRGTGACCWG SEQ ID NO: 2.

The pK7C3 vector is a pHEN4 (Ghahroudi et al, 1997, *FEBS letters*, 414: 521–526) derivative where the ampicillin resistance gene was replaced by the chloramphenicol resistance gene and the haemaglutinin tag was replaced by a histidine and c-myc tag (Ghahroudi et al, 1997, *FEBS letters*, 414: 521–526)
Construction of M13 Pseudovirions Displaying Camel VHH VHH's from the CAMELB library were expressed on phage after infection of the library with M13KO7 helper phage (pK7C3-VHHB) as described by Ghahroudi et al, 1997, *FEBS letters*, 414: 521–526. A library of $3 \times 10^6$ individual colonies was obtained of which 85% had the correct insert size, and 90% of these could produce a fusion protein between VHH and pIII.
Selection of Ovalbumin Specific Pseudovirions by Biopanning The CAMELB library was panned for the presence of binders on ovalbumin coated in wells of microtitre plates (10 µg ovalbumin/well). Bound phages were eluted and allowed to infect TG1 cells (Stratagene). After two or three rounds of panning, individual colonies were grown, periplasmic extracts were prepared and screened for the presence of ovalbumin binders in ELISA. (Skerra and Pluckthun, 1988, *Science*, 240: 1038–1041). The plasmid of these binders was prepared and sequenced. We obtained 2 VHH binders of which 1DBOVA1 (DVQLVESGGGSVPAGSLRLSCAVSG YTYENRYMAWFRQAPGKEREGVAAIWRGGNNPYY ADSVKGRFTISQDNAKNIVSLLMNSLKPEDTAIYYCA AQAGRFSGPLYESTYDYWGQGTQVTVSS SEQ ID NO:3) was the most abundant.
Titre Determination The titre of the phages was determined by incubation of 150 µl TG1 (F$^+$) cells at OD600nm=0.5 with 10 µl of phages of different dilutions, for 30 minutes at 37° C.

This was plated on LB-agar plates containing 25 µg/ml chloramphenicol and 2% glucose.

The background for infection of DH5α(Gibco BRL) was determined under the same conditions as described above for TG1.
Preparation of the Phages Cultures of TG1 containing pK7C3-VHHB or 1DBOVA1 were grown at 37°C. in 100 ml 2×TY medium containing 2% glucose, and 25 µg/ml chloramphenicol, until the OD600nm reached 0.5. M13KO7 phages ($10^{12}$) were added and the mixture was incubated in a water bath at 37° C. for 2×30 minutes, first without shaking, then with shaking at 100 rpm. The culture was centrifuged (15', 4300 rpm, room temperature). The bacterial pellet was dissolved in 600 ml of 2×TY medium containing 25 µg/ml chloramphenicol and 25 µg/ml kanamycin, and incubated overnight at 300° C., vigorously shaking at 250 rpm.

These overnight cultures were centrifuged for 15 minutes at 4300 rpm at 4° C. Phages were precipitated for 1 hour on ice with PEG (20% poly-ethylene-glycol and 1.5 M NaCl), pelleted by centrifugation (30', 4300 rpm, 4° C.), dissolved in 10 ml PBS and centrifuged for another 10 minutes at 4300 rpm and 4° C. The supernatant was loaded on 2 ml Ni-NTA (QIAGEN), washed extensively with 50 mM Na$_2$HPO$_4$, 1M NaCl pH=7.0, eluted with 50 mM NaAc, 1M NaCl pH=4.5 and neutralised with 1 M Tris pH=7.4. Phages were again PEG precipitated by immediate centrifugation for 30 minutes at 4300 rpm and 4° C. after PEG addition. The pellet (invisible) was dissolved in 1 ml PBS+100 µl PBS-caseine. 15% glycerol was added and the phages were stored at −80° C. for maximally 1 week, until further use.

Example II

Display of Oprl and Oprl-ovalbumin Fusion Protein on E. coli

The ptrc-Oprl (Cote-Sierra et al., 1998, Gene, 221:25–34; FIG. 3) or ptrc-Oprl-ova (obtained by amplifying the gene encoding for hen-egg ovalbumin, digesting the product with BamHI and EcoRI and cloning the digest in BglII/EcoRI digested ptrc-Oprl) plasmids were transformed in E.coli Top10F' (Invitrogen) and tested for expression in M9CAA and LB-medium in Western blot. Cells were induced with 1 mM ITPG (Calbiochem) at OD600nm=0.6 and grown overnight at 37° C. on a rotary shaker at 200 rpm. Cells were centrifuged and concentrated 10-fold. Total cell lysates, obtained by sonication were loaded on a 12% SDS-PAGE and transferred to nitrocellulose for Western blotting. Transferred proteins were detected using a monoclonal anti-Oprl antibody QB2 (De Vos D. et al, Journal of general microbiology 1993, 139: 2215–2223). An anti-mouse IgG conjugated with alkaline phosphatase (Sigma) was applied and the blots were developed with the BCIP/NBT substrate. The results are shown in FIG. 4. A band at the position of intact fusion protein is clearly observed. However, large amounts of degradation products demonstrate the instability of the pOprl-ova form. Since these degradation products might interfere with the infection, conditions for growth and infection were optimised, amongst others by the use of UT5600 (F−, ara-14, leuB6, azi-6, lacY1, proC14, tsx-67, entA403, trpE38, rfbD1, rpsL109, xyl-5, mtl-1, thi1, Δ ompT, fepC266) (Biolabs). UT5600 is an outer membrane protease T-deficient E. coli strain, which was used for the stable presentation of Ig scFv fusions (Maurer and Meyer, J. Bacteriol., 1997, 179: 794–804).

Example III

Receptor Independent Entering of E.coli by M13 Pseudovirions

Cultures of E.coli strain DH5α containing ptrc-Oprl (Cote-Sierra et al, 1998, Gene, 221: 25–34) or ptrc-Oprl-OVA (indicated as DH5α{ptrc-Oprl-OVA}) were incubated at 37° C. at 220 rpm until the OD600nm reached 0.6. Cells were centrifuged at 4300 rpm for 5 minutes and resuspended in the original volume and in the same medium (=washed cells*). A fraction of the cells was induced with 1 mM IPTG and grown at 37° C. for another 4 hours (**).

To test the pilus independent entering of E.coli displaying ovalbumin on its surface by M13 phages displaying ovalbumin specific antibodies, we incubated 150 µl of E.coli cells with 10 µl phages from pK7C3-VHHB of different dilutions for 1 hour at 37° C. without shaking.

Infection of E. coli was screened for by selection of incubation mixtures on LB-agar plates containing 100 µg/ml ampicillin, 25 µg/ml chloramphenicol and 2% glucose.

Individual colonies were screened in ELISA. Therefore, large single colonies (resistant to ampicillin and chloramphenicol) were inoculated in 10 ml TB medium containing 0.1% glucose, 100 µg/ml ampicillin and 25 µg/ml chloramphenicol for 8 hours. IPTG was added at a final concentration of 10 mM and the cultures were grown overnight at 37° C. at 200 rpm.

Individual colonies in TG1 and DH5α were picked and grown in 10 ml TB medium containing 0.1% glucose and 25 µg/ml chloramphenicol for 4 hours. IPTG was added at a final concentration of 1 mM and the cultures were grown overnight at 28° C. at 200 rpm.

Periplasmic fractions were prepared by pelleting the overnight cultures, and dissolving the pellet in 200 µl TES (0.2 M Tris-HCl, pH=8.0, 0.5 mM EDTA, 0.5 M sucrose). This was incubated on ice for 20 minutes. 300 µl TES/4 was added and incubated at 4° C. for 25 minutes. This suspension was centrifuged for 25 minutes at maximal speed in an eppendorf centrifuge and the supernatant was used for testing in ELISA.

Periplasmic fractions were tested in NUNC-plates coated overnight with ovalbumin (5 µg/ml) or casein as a negative control (1% w/v in PBS) and blocked overnight with 1% (w/v) casein. Samples were incubated for 2 hours at room temperature and ovalbumin binding VHH's were detected with a mouse anti-Histidine-tag (SEROTEC), anti-mouse-alkaline phosphatase conjugate (Sigma) and a chromogenic substrate (Sigma). The results are summarised in Table I

TABLE 1

|  | Positives in ELISA |
| --- | --- |
| TG1 | 1/337 |
| DH5α | 0/7 |
| DH5α + ptrc-Oprl | 2/141 |
| DH5α{ptrc-Oprl-OVA} | 7/16, 17/38, 7/24 |
| DH5α{ptrc-Oprl-OVA}, washed* | 14/19 |
| DH5α{ptrc-Oprl-ova} + IPTG** | 3/12 |

Table 1:
The numbers indicate the number of positive clones in ELISA versus the number of clones that were tested.
Extracts were scored positive if the OD405 nm was at least double the OD of the background (coated caseine at 1%).
Numbers separated by a comma are from independent experiments.
*The cells were washed 1 time with fresh medium before infection with phages as described above.
**Cells were induced with IPTG as described above.

Example IV

Receptor Independent Entering of E.coli by Pseudovirions is Specific for the Artificial Receptor 150 µl of washed UT5600 containing ptrc-Oprl-OVA (indicated as UT5600{ptrc-Oprl-OVA}) or DH5α{ptrc-Oprl-OVA} cells at OD600nm=0.6 were incubated with 10 µl phages of pK7C3-VHHB of different dilutions for 1 hour at 37° C. without shaking.

The same experiment was repeated after pre-incubation of the phages with 1ml ovalbumin (2 mg/ml) for 1 hour at room temperature. The phages were mixed with 150 µl of washed UT5600{ptrc-Oprl-OVA} or DH5α{ptrc-Oprl-OVA} cells at OD600nm=0.6 and incubated for 1 hour at 37° C.

This was plated on LB agar plates containing 25 µg/ml chloramphenicol, 100 µg/ml ampicillin and 2% glucose. Expression of 25–45 clones in UT5600 cells and DH5α was carried out as described above.

The results are summarised in Table 2.

TABLE 2

|  | DH5α c$^r$, a$^r$ | UT5600 c$^r$, a$^r$ |
| --- | --- | --- |
| E. coli (ptrc-Oprl-ova) + pK7C3-VHHB phages | 150 | 90, 73 |

TABLE 2-continued

|  | DH5α c$^r$, a$^r$ | UT5600 c$^r$, a$^r$ |
|---|---|---|
| E. coli (ptrc-Oprl-ova) + ovalbumin pretreated pK7C3-VHHB phages | 1 | 2, 2 | number of colonies on plates after infection of washed UT5600{ptrc-Opri-OVA} or DH5α{ptrc-Oprl-OVA} cells with phages with or without pre-incubation with ovalbumin. Numbers separated by a commaare from independent experiments.
c$^r$: chloramphenicol resistant;
a$^r$: ampicillin resistant Infection of washed UT5600{ptrc-Oprl-OVA} or DH5α{ptrc-Oprl-OVA} cells with phages from pK7C3-VHHB pre-incubated with hen-egg ovalbumin protein, reduced the number of transformants significantly, which means that infection is dependent upon ovalbumin display on the host cell wall.

Example V

Survival of E.coli Cells and Phages Upon Coincubation

150 µl of washed UT5600{ptrc-Oprl-OVA} or DH5α{ptrc-Oprl-OVA} cells at OD600nm=0.6 were incubated with 10 µl phages of PK7C3-VHHB for 1 hour at 37° C. without shaking.

This was plated on LB agar plates containing 25 µg/ml chloramphenicol, 100 1µg/ml ampicillin and 2% glucose (C).

Cells were also checked for survival upon growth (A) and upon incubation with phages (B) by dilution and plating on LB agar plates containing 100 µg/ml ampicillin and 2% glucose. The results are shown in Table 3.

TABLE 3

| number of cells | DH5α | UT5600 |
|---|---|---|
| Before incubation (A) | 2 × 10$^8$ | 10$^9$ |
| After incubation (B) | 5 × 10$^7$ | 3 × 10$^8$ |
| entered (C) | 64 | 150 |

Table 3:
Number of cells upon incubation of washed UT5600{ ptrc-Oprl-OVA}_or DH5α{ptrc-Oprl-OVA} cells with pK7C3-VHHB phages.

The titre of pK7C3-VHHB phages was determined before incubation with washed DH5α{ptrc-Oprl-OVA} cells. Cells were centrifuged after incubation for 1 hour at 37° C. and the supernatant was used to determine the titre of unentered phages. The titres were determined by incubation of 150 µl TG1 cells at OD600nm=0.5 with 10 µl of phages of different dilutions for 30 minutes at 37° C. This was plated on LB-agar plates containing 25 µg/ml chloramphenicol and 2% glucose. The number of transformants are listed in Table4.

TABLE 4

|  | number of phages |
|---|---|
| Before incubation | 5.6 × 10$^7$ |
| After incubation | 1.2 × 10$^7$ |

Table 4:
Number of pK7C3-VHHB phages before and after incubation with washed DH5α{ptrc-Oprl-OVA} cells UT5600{ptrc-Oprl-OVA} or DH5α{ptrc-Oprl-OVA} cells survived very well when incubated with and entered by pK7C3-VHHB phages. The pK7C3-VHHB phages which did not enter UT5600{ptrc-Oprl-OVA} or DH5α{ptrc-Oprl-OVA} cells are still able to infect TG1 cells and are therefore stable under the conditions used.

Example VI

Individual E.coli Cells Displaying Ovalbumin on the Surface are Entered by a Single Ovalbumin Specific Phage Positive clones were selected from experiment 2 for UT5600 (clone number 10, 11, 12, 13, 16, 17). They were inoculated in 5 ml LB containing 25 µg/ml chloramphenicol, and grown overnight at 37° C. Plasmid was prepared, transformed in TG1 and plated on LB agar plates containing 25 µg/ml chloramphenicol and 2% glucose. Individual colonies were tested in ELISA as described before (in TB containing 25 µg/ml chloramphenicol and 0.1% glucose).

TABLE 5

|  | Positives in ELISA |
|---|---|
| 10 | 8/8 |
| 11 | 8/8 |
| 12 | 8/8 |
| 13 | 7/8 |
| 16 | 8/8 |
| 17 | 8/8 |

Table 5:
number of positive clones in ELISA versus the number of clones that were tested for individual colonies.

Individual positive clones were selected and grown overnight for plasmid preparation. After transformation in TG1 individual colonies were tested in ELISA. All clones scored positive, therefore we can be sure that ovalbumin specific phages have entered the cell. Colony PCR on these individual colonies showed that they have the same length if they originate from the same original clone.

Example VII

Optimisation of the Conditions of Receptor Independent Entering

Cell of DH5α{ptrc-Oprl-OVA} and UT5600{ptrc-Oprl-OVA} were grown at 37° C. A 150 µl sample was removed at different time intervals, washed and 5×10$^8$ phages of pK7C3-VHHB were added. This suspension was incubated for 1 hour at 37° C. and plated on LB-agar plates with 2% glucose, 25 µg/ml chloramphenicol and 100 µg/ml ampicillin. Single colonies were tested in ELISA as described above. The results are shown in Table 6a and 6b.

TABLE 6a

| | UT5600 | | |
|---|---|---|---|
| Time of growth (minutes) | OD600 nm | tfu | Positives in ELISA pK7C3-VHHB |
| 30 | 0.062 | 20 | 7/15 |
| 60 | 0.076 | 56 | 7/15 |
| 90 | 0.142 | 100 | 11/15, 2/3 |
| 120 | 0.273 | 130 | 11/16 |
| 150 | 0.555 | 150 | 8/15 |

TABLE 6a-continued

UT5600

| Time of growth (minutes) | OD600 nm | tfu | Positives in ELISA pK7C3-VHHB |
|---|---|---|---|
| 210 | 1.24 | 120 | 2/13 |
| 270 | 2.25 | 30 | 7/12 |

Tables 6a and 6b:
Number of positive clones in ELISA versus the number of clones that were tested and the number of transformants (tfu) as a function of the OD600 nm of the cells.
Numbers separated by a comma are from independent experiments.

TABLE 6b

DH5α.

| Time of growth (minutes) | OD600 nm | tfu | Positives in ELISA pK7C3-VHHB |
|---|---|---|---|
| 60 | 0.010 | 0 | — |
| 120 | 0.038 | 23 | 5/13 |
| 210 | 0.197 | 97 | 3/8 |
| 270 | 0.600 | 84 | 3/5 |
| 300 | 0.665 | 64 | 2/8 |

Table 6a and 6b:
Number of positive clones in ELISA versus the number of clones that were tested and the number of transformants (tfu) as a function of the OD600 nm of the cells.
Numbers separated by a comma are from independent experiments.

Cell of DH5α{ptrc-Oprl-OVA} and UT5600{ptrc-Oprl-OVA} were grown at 37° C. Increasing concentrations of pK7C3-VHHB phages were added to 150 μl of washed cells at OD600nm=0.2–0.3 for UT5600{ptrc-Oprl-OVA} and 0.6 for DH5α{ptrc-Oprl-OVA}. This mixture was incubated for 1 hour at 37° C. and plated on LB-agar plates with 2% glucose, 25 μg/ml chloramphenicol (Chl) and 100 μg/ml ampicillin (Amp). Single colonies were tested in ELISA as described before.

TABLE 7a

UT5600.

| Number of phages added | Number of transformants on Amp/Chl | Number of positives in ELISA | Number of positives in ELISA (%) |
|---|---|---|---|
| 7 × 10$^6$ | 30 | 0/2 | — |
| 1 × 10$^7$ | 20 | 0/2 | — |
| 7 × 10$^7$ | 85, 90, 150 | 0/5, 1/24, 2/24 | —, 4, 8 |
| 1 × 10$^8$ | 70 | 1/4 | 25 |
| 4 × 10$^8$ | 67 | 4/29 | 14 |
| 7 × 10$^8$ | 300, 300 | 18/24, 20/20 | 75, 100 |

Table 7a–b:
Increasing concentrations of pK7C3-VHHB phages were mixed with 150 μl UT5600{ptrc-Oprl-OVA} at OD600 nm = 0.2–0.3 or with DH5α{ptrc-Oprl-OVA} cells at OD600 nm = 0.6. Individual colonies were tested in ELISA.
Numbers separated by a comma are from independent experiments.
Optimal conditions for uptake of phages were tested by mixing pK7C3-VHHB phages with UT5600{ptrc-Oprl-OVA} or DH5α{ptrc-Oprl-OVA} cells at different optical densities. Individual colonies were tested in ELISA.
For UT5600{ptrc-Oprl-OVA} the optimal density is between 0.15 and 0.3 and for DH5α{ptrc-Oprl-OVA} between 0.2 and 0.6.

TABLE 7a-continued

UT5600,

| Number of phages added | Number of transformants on Amp/Chl | Number of positives in ELISA | Number of positives in ELISA (%) |
|---|---|---|---|

UT5600{ptrc-Oprl-OVA} cells grow much faster than DH5α{ptrc-Oprl-OVA} and are easier infected by anti-ovalbumin expressing phages (positive clones in ELISA) (73% versus 30–50% table6a–b).
When increasing amounts of phages were mixed with UT5600[ptrc-Oprl-OVA] cells (OD600 nm = 0.2–0.3), more positive clones were obtained in ELISA (table7a).
75–100% positive clones were obtained when 5–10 × 10$^8$ phages were mixed with 0.5 × 10$^8$ UT5600{ptrc-Oprl-OVA} cells resulting in 150–500 individual colonies.
However, in DH5α{ptrc-Oprl-OVA}, no increase in positive clones in ELISA was observed upon addition of increasing amounts of phages (table7b).

TABLE 7b

DH5α.

| Number of phages added | Number of transformants on Amp/Chl | Number of positives in ELISA | Number of positives in ELISA (%) |
|---|---|---|---|
| 5 × 10$^7$ | 85 | 10/28 | 36 |
| 2 × 10$^8$ | 250 | 21/43 | 49 |
| 5 × 10$^8$ | 110 | 17/40 | 43 |

Table 7a–b:
Increasing concentrations of pK7C3-VHHB phages were mixed with 150 μl UT5600{ptrc-Oprl-OVA} at OD600 nm = 0.2–0.3 or with DH5α{ptrc-Oprl-OVA} cells at OD600 nm = 0.6. Individual colonies were tested in ELISA.
Numbers separated by a comma are from independent experiments.
Optimal conditions for uptake of phages were tested by mixing pK7C3-VHHB phages with UT5600{ptrc-Oprl-OVA} or DH5α{ptrc-Oprl-OVA} cells at different optical densities. Individual colonies were tested in ELISA.
For UT5600{ptrc-Oprl-OVA} the optimal density is between 0.15 and 0.3 and for DH5α{ptrc-Oprl-OVA} between 0.2 and 0.6.
UT5600{ptrc-Oprl-OVA} cells grow much faster than DH5α{ptrc-Oprl-OVA} and are easier infected by anti-ovalbumin expressing phages (positive clones in ELISA) (73% versus 30–50% table6a–b).
When increasing amounts of phages were mixed with UT5600[ptrc-Oprl-OVA] cells (OD600 nm = 0.2–0.3), more positive clones were obtained in ELISA (table7a).
75–100% positive clones were obtained when 5–10 × 10$^8$ phages were mixed with 0.5 × 10$^8$ UT5600{ptrc-Oprl-OVA} cells resulting in 150–500 individual colonies.
However, in DH5α{ptrc-Oprl-OVA}, no increase in positive clones in ELISA was observed upon addition of increasing amounts of phages (table7b).

Example VIII

Selective Elimination by Killer Phages

Barnase is a extracellular ribonuclease from *Bacillus amyloliquefaciens* (Hartley & Rogerson 1972, Prep. Biochem. 2: 229–242). A very low level of intracellular expression of barnase in *E.coli* is lethal because barnase depolymerizes the RNA of its host. Jucovic & Hartley developed a tightly controlled system (pMI47a) for the intracellular expression of barnase in *E.coli* (*Protein engineering*, 8: 497499, 1995). The plasmid encodes barstar (a strong polypeptide inhibitor of barnase) under the transcriptional control of the Tac promotor. A barnase gene (without secretion signal) has been cloned in the inverse orientation downstream from barstar. In pMI47a, the Tac promotor is followed by attP, followed by barstar, followed by the inversed gene for barnase, followed by attB. AttP and attB are derived from the phage lambda attachment site. pMI47a is not toxic for *E.coli* because it overproduces barstar and no barnase (OFF configuration, FIG. 5a). The Integrase protein (INT function) from phage lambda recognises the attB and attP sequences and inverses the DNA fragment that is located between the attB and attP sites in vivo. In the resulting plasmid pMI47b the Tac promotor is followed by attR, followed by barnase, followed by the inversed gene for barstar, followed by attL. Sites attR and attL are the products of recombination between attP and attB (Jucovic & Hartley, 1995, Protein Engineering 8: 497499). This plasmid is toxic for E.coli because it produces active barnase in the cytoplasm of the host (ON configuration, FIG. 5b). The system can be switched in vivo from the OFF to the ON configuration in the E.coli strain D1210HP (supE44 ara14 galK2 lacY1 D(gpt-proA)62 rpsL20 (Str$^r$) xyl-5 mtl-1 recA13 D(mrcC-mrr)HsdS$^-$(r$^-$m$^-$) lacl$^q$ LacY$^+$Ixis-kil-cI857) (Stratagene) by a short incubation at 42° C. This strain encodes the integrase function (Int; Ixis) from phage lambda, whereas D1210 doesn't have this function.

A conditionally lethal phage particle was made by cloning the conditionally lethal cassette of pMI47a into a phagemid. A DNA fragment of pMI47a including the Tac promotor, followed by attP, followed by barstar, followed by the inversed gene for barnase, and followed by attB was amplified by PCR. This PCR product was cloned as a blunt end fragment within the EcoRI site of the pK7C3-1DBOVA1 vector (example 1) to give pK7C3BB-1DBOVA1 (Before ligation, pK7C3-1DBOVA1 was linearized with EcoRI and filled-in with Klenow DNA polymerase).

Plasmids of pK7C3BB-1DBOVA1, pK7C3, ptrc-Oprl-OVA and pM147a were transformed in D1210 and D1210HP electrocompetent cells. Individual colonies were grown in LB with 25 µg/ml chloramphenicol or 100 µg/ml ampicillin and 2% glucose at 37° C. until the OD600nm= 1.2–1.3. Half of the culture was exposed to thermal induction (15 minutes at 420° C.). Both fractions (before and after induction) were spread after appropriate dilutions, on LB agar plates containing 25 µg/ml chloramphenicol or 100 µg/ml ampicillin and 2% glucose. The numbers of the transformants were counted and are listed in table 8.

TABLE 8

Number of transformants with or without thermoinduction of D1210 or D1210HP cells containing PMI47a, ptrc-Oprl-OVA, pK7C3 or pK7C3BB-1DBOVA1.

| construct | E. coli strain | temperature | Number of transformants/ml |
|---|---|---|---|
| PMI47a | D1210 | 37° C. | 3 × 10$^8$ Amp$^r$ |
| | | 37° C.–42° C. | 2 × 10$^8$ Amp$^r$ |
| | D1210HP | 37° C. | 2 × 10$^8$ Amp$^r$ |
| | | 37° C.–42° C. | 280 Amp$^r$ |
| Ptrc-Oprl-OVA | D1210 | 37° C. | 3 × 10$^8$ Amp$^r$ |
| | | 37° C.–42° C. | 2 × 10$^8$ Amp$^r$ |
| | D1210HP | 37° C. | 3 × 10$^8$ Amp$^r$ |
| | | 37° C.–42° C. | 2 × 10$^8$ Amp$^r$ |
| pK7C3 | D1210 | 37° C. | 5 × 10$^8$ Chl$^r$ |
| | | 37° C.–42° C. | 4 × 10$^8$ Chl$^r$ |
| | D1210HP | 37° C. | 6 × 10$^8$ Chl$^r$ |
| | | 37° C.–42° C. | 3 × 10$^8$ Chl$^r$ |
| pK7C3BB-1DBOVA1 | D1210 | 37° C. | 4 × 10$^8$ Chl$^r$ |
| | | 37° C.–42° C. | 3 × 10$^8$ Chl$^r$ |
| | D1210HP | 37° C. | 5 × 10$^8$ Chl$^r$ |
| | | 37° C.–42° C. | 560 Chl$^r$ |

The results show that D1210 cells (lacking the Int gene) transformed with PM147a, ptrc-Oprl-OVA, pK7C3 or pK7C3BB-1DBOVA1 survive well upon thermoinduction, which indicates that PMI47a, ptrc-Oprl-OVA, pK7C3 and pK7C3BB-1DBOVA1 are not harmful for E.coli. PMI47a, ptrc-Oprl-OVA, pK7C3 and pK7C3BB-1DBOVA1 can be transformed and maintained in D1210HP if the cells are maintained at 37° C. (OFF configuration). However, when cells are incubated at 42° C. for 15 minutes (ON configuration), the integrase function is activated, and D1210HP cells containing PMI47a or pK7C3BB-1DBOVA1 do not longer survive. These experiments show that the phagemid pK7C3BB-1DBOVA1 is toxic for E.coli strain D1210HP if inversion is induced by thermoinduction of the Int gene.

Elimination Upon Recognition of an Artificial Receptor

D1210 and D1210HP electrocompetent cells were transformed with ptrc-Oprl-OVA. A single colony was used to inoculate a culture in LB containing 100 µg/ml ampicillin. Phages of pK7C3-1DBOVA1 or pK7C3BB-1DBOVA1 were prepared as described above, 150 µg/ml of washed cells were incubated with 5×10$^8$ pK7C3-1DBOVA1 or pK7C3BB-1DBOVA1 phages for 1 hour at 37° C. Half of these mixtures were exposed to thermal induction (15 minutes at 42° C.). An aliquot (before and after induction) was spread on LB agar plates containing 25 µg/ml chloramphenicol and 100 µg/ml ampicillin and 2% glucose. The numbers of transformants were counted and are listed in table 9.

TABLE 9

Number of transformants when D1210 or D1210HP cells containing ptrc-Oprl-OVA were incubated with pK7C3-1DBOVA1 or pK7C3BB-1DBOVA1 phages with or without thermal incubation.

| type of phages | E. coli strain | temperature | Number of transformants |
|---|---|---|---|
| pK7C3-1DBOVA1 | D1210 | 37° C. | 8000 |
| | | 37° C.–42° C. | 7800 |
| | D1210HP | 37° C. | 8100 |
| | | 37° C.–42° C. | 8300 |
| pK7C3BB-1DBOVA1 | D1210 | 37° C. | 7800 |
| | | 37° C.–42° C. | 7900 |
| | D1210HP | 37° C. | 7600 |
| | | 37° C.–42° C. | 2 |

D1210HP cells displaying ovalbumin on their surface are killed by pseudovirions containing phagemid pK7C3BB-1DBOVA1 after thermoinduction. This experiment clearly demonstrates that coli cells, expressing an artificial receptor can be recognised and killed by a bacteriophage with an artificial ligand that recognises the artificial receptor.

Example IX

Library Versus Library Screening ("Picup" Screening)

Fission yeast (Schizosaccharomyces pombe p2, h$^+$, arg$^{3-}$, ura$^{4-}$) was grown in YES medium (0.5% (w/v) yeast extract, 3.0% .(w/v) glucose +225 mg/l adenine, histidine, leucine, uracil and lysine hydrochloride). Cells were harvested by low speed centrifugation. 15 g wet cells were washed with 100 ml S-buffer (1.4 M sorbitol, 40 mM HEPES, 0.5 mM MgCl$_2$ adjusted to pH 6.5). After centrifugation the pellet was resuspended in 100 ml S-buffer containing 10 mM 2-mercaptoethanol and 1 mM PMSF and incubated at 30° C. for 10 minutes. After centrifugation, the pellet was resuspended in 60 ml S-buffer containing 1 mM PMSF, and 460 mg Zymolase 20T (ICN Biomedicals) was added to prepare spheroplasts. After incubation for 3 hours at 30° C., the pellet was washed five times with 100 ml S-buffer containing 1 mM PMSF. Spheroplasts were resuspended in 60 ml Tris (25 mM, pH=7.5), 100 mM NaCl, 2 mM EDTA supplemented with 1 tablet protease inhibitor mix (Boehringer) and lysed by two passages in French press. The supernatant was recovered after centrifugation for 30 minutes at 15.000 rpm in SS34 rotor. 15.5 g solid ammonium-sulfate was added to 30 ml of the supernatant. After incubation on ice for 1 hour, precipitated material was recovered by centrifugation and resuspended in 20 ml PBS. The solution was equilibrated in PBS by passage over PD10 columns. Following this treatment, the protein concentration was determined with Bio-Rad protein assay kit, using BSA as reference protein. Six aliquots, each 5 ml in volume, with a protein concentration of 8 mg/ml, were prepared for camel immunisation.

The immunisation and blood withdrawal scheme is as follows:

| Day | |
|---|---|
| Day 0 | Collect preimmune serum |
| Day 0 | inject subcutaneously 1 tube (40 mg protein) + complete freund adjuvant |
| Day 7 | inject subcutaneously 1 tube + incomplete freund adjuvant |
| Day 14 | inject subcutaneously 1 tube + incomplete freund adjuvant |
| Day 21 | Collect anticoagulated blood and serum |
| Day 21 | inject subcutaneously 1 tube + incomplete freund adjuvant |
| Day 28 | inject subcutaneously 1 tube + incomplete freund adjuvant |
| Day 35 | inject subcutaneously 1 tube + incomplete freund adjuvant |
| Day 38 | Collect anticoagulated blood and serum |

A cDNA library of *Schizosaccharomyces pombe* is constructed by recloning the S.pombe cDNA bank that is used in Two-hybrid system (Clontech). The cDNA inserts are amplified with specific primers harbouring restriction enzyme sites compatible for cloning into the multiple cloning site of ptrc-Oprl. The library is transformed in UT5600 or in D1210HP electro-competent cells.

The serum immunoglobulins from the immunised animal (day 21 or 38) are passed over protein A and protein G columns to purify the conventional antibodies and the heavy chain antibodies. Each fraction is used in a Western blot to evaluate the presence and titre of anti-*S.pombe* protein immunoglobulins.

Peripheral blood lymphocytes from the immunised camel are prepared using Unisep (WAK Chemie, Germany) from the anticoagulated blood isolated at days 21and 42. The camel heavy chain antibodies (VHH's) from $10^7$ lymphocytes are ligated after RT-PCR amplification in the Sfil-Notl sites of the pK7C3 or pK7C3-BB (pK7C3 with the barnase-barstar inversion system) vector and transformed in TG1 as described above, in order to obtain a library of $10^8$ individual clones. The VHH phages is prepared by infection of the *E.coli* culture with M13K07 and enriched for virons with a VHH-gpIII fusion by IMAC chromatography (see before).

For the PICUP experiment, $10^7$–$10^8$ UT5600 cells from the cDNA library of *S.pombe* are mixed with $10^{12}$ phages obtained from the camel VHH library. The mixture is incubated for 1 hour at 37° C. and plated on LB agar plates containing 100 µg/ml ampicillin, 25 µg/ml chloramphenicol and 2% glucose. Colonies can only grow on this medium if the UT5600 cells are expressing a *S.pombe* antigen that is recognised and subsequently infected by a virion carrying an antigen-specific VHH. For each colony the VHH insert is sequenced with a primer annealing in the gene pIII sequence, while the cDNA coding for the antigen is directly sequenced with an Oprl specific primer. The latter sequence is screened in a BLAST on the *S.pombe* genome sequence database to identify the gene. The specificity of the VHH (having a his-tag) is also tested in a Western blot in which the *S.pombe* extracted proteins are separated on SDS gels. The presence of the VHH is revealed with an anti-His monoclonal antibody (SEROTEC).

As a positive control, individual colonies from the cDNA library are used in a separate PICUP experiment. One single clone that is capable to produce a fusion protein with the lipoprotein (as seen by Western blot) is grown and challenged with the VHH phages from the library. The VHH from clones growing on Ampicilline and Chloramphenicol are induced with IPTG, extracted from the periplasm and it's binding to the yeast protein tested in Western blot and ELISA.

To eliminate particular antigens dominantly present in the matched pairs (*S.pombe* antigen—specific VHH) or particular VHH over-represented in the matched pairs, the killer phage strategy is used. To this end the UT5600 cells carrying the *S.pombe* cDNA library are incubated with the phages from the pK7C3-BB library of VHH. After infection the suspension is incubated at 42° C. to eliminate the *E.coli* cells that are infected with phages. The surviving cells are carrying *S.pombe* antigens that are less frequent represented in the ptrc-Oprl or pK7C3-BB libraries. In a second step these surviving cells are used to inoculate fresh medium and to restart the PICUP experiment as before.

What is claimed is:

1. A genetically modified bacteriophage or a phagemid capable of entering a host cell, said genetically modified bacteriophage or phagemid comprising an artificial ligand, wherein said artificial ligand specifically binds to m artificial receptor expressed by said host cell, whereby interaction with and/or entering of said host cell by said genetically modified bacteriophage or phagemid is pilus-independent.

2. The genetically modified bacteriophage or phagemid according to claim 1, wherein said bacteriophage or phagemid is not dependent upon OmpA, OmpC, OmpF, Ttr, or pilin for interacting with or entering said host cell.

3. The genetically modified bacteriophage or phagemid according to claim 1, wherein the binding of said genetically modified bacteriophage or phagemid is mediated by an antigen—antibody reaction.

4. The genetically modified bacteriophage or phagemid according to claim 1, where said bacteriophage is M13.

5. The genetically modified bacteriophage or phagemid according to claim 1, in which the phagemid is a pK7C3 derived vector.

6. The genetically modified bacteriophage or phagemid according to claim 3, in which the antibody is a camelid derived antibody, or is a functional fragment thereof, including a fragment comprising all or part of the VHH chain of a camelid heavy chain antibody.

7. The genetically modified bacteriophage or phagemid of claim 1, wherein said genetically modified bacteriophage or phagemid comprises a nucleic acid encoding said artificial ligand such that said artificial ligand is at the surface of said genetically modified bacteriophage or phagemid.

8. The genetically modified bacteriophage or phagemid of claim 6, said functional fragment comprising all or part of the VHH chain of a camelid heavy chain antibody.

9. The genetically modified bacteriophage or phagemid of claim 1, wherein said artificial ligand is fused to a polypeptide comprising sequences that are normally involved in natural receptor recognition.

10. The genetically modified bacteriophage or phagemid of claim 9, wherein said sequences that are normally involved in natural receptor recognition comprise pIII or the D2 domain of pIII.

* * * * *

UNITED STATES PATENT AND TRADEMARK OFFICE
CERTIFICATE OF CORRECTION

PATENT NO.    : 6,479,280 B1
DATED         : November 12, 2002
INVENTOR(S)   : Karen Silence et al.

It is certified that error appears in the above-identified patent and that said Letters Patent is hereby corrected as shown below:

<u>Title page,</u>
Item [56], References Cited, OTHER PUBLICATIONS, delete "Glahroudi" and insert -- Ghahroudi -- therefor.
Item [74], *Attorney, Agent, or Firm*, please delete "RIchardson" and insert -- Richardson -- therefor.

<u>Column 19,</u>
Line 40, please delete "m" and insert -- an -- therefor.

Signed and Sealed this

Thirteenth Day of April, 2004

JON W. DUDAS
*Acting Director of the United States Patent and Trademark Office*